(12) United States Patent
Simard et al.

(10) Patent No.: US 6,592,561 B2
(45) Date of Patent: Jul. 15, 2003

(54) SANITARY ABSORBENT ARTICLE HAVING A TEAR-RESISTANT FLANGE SEAL

(75) Inventors: Jean-Sebastien Simard, Quebec (CA); Henri Brisebois, Quebec (CA)

(73) Assignee: Johnson & Johnson, Inc. (CA)

( * ) Notice: Subject to any disclaimer, the term of this patent is extended or adjusted under 35 U.S.C. 154(b) by 120 days.

(21) Appl. No.: 09/823,040

(22) Filed: Mar. 30, 2001

(65) Prior Publication Data

US 2002/0143314 A1 Oct. 3, 2002

(51) Int. Cl.[7] ............................... A61F 13/15
(52) U.S. Cl. ..................... 604/385.04; 604/385.03; 604/386
(58) Field of Search ................ 604/385.01, 385.04, 604/385.03, 385.05, 386

(56) References Cited

U.S. PATENT DOCUMENTS

| | | | | |
|---|---|---|---|---|
| 5,681,303 A | * | 10/1997 | Mills et al. | 604/385.2 |
| 5,993,431 A | * | 11/1999 | McFall et al. | 604/385.2 |
| 6,176,850 B1 | * | 1/2001 | Rosenfeld et al. | 604/389 |
| 6,280,428 B1 | * | 8/2001 | Lash et al. | 604/385.04 |
| 6,328,723 B1 | * | 12/2001 | Burns, Jr. et al. | 604/385.22 |
| 6,358,234 B1 | * | 3/2002 | Terada et al. | 604/385.04 |

FOREIGN PATENT DOCUMENTS

| WO | WO 99/16397 | * | 4/1999 | A61F/13/15 |
|---|---|---|---|---|

* cited by examiner

*Primary Examiner*—Weilun Lo
*Assistant Examiner*—Jacqueline F Stephens

(57) ABSTRACT

A sanitary absorbent article such as a sanitary napkin, or incontinence pad having a cover layer that is fluid permeable, an absorbent system and a liquid-impervious barrier layer under the absorbent system to prevent collected liquid to escape therefrom. The fluid-permeable cover layer is attached to the liquid-impervious barrier layer to form a flange seal enclosing the absorbent system. The flange seal includes two zones, namely a first zone and a second zone separated by a common boundary, each zone manifesting different mechanical properties. The first zone that resides closer to the outer edge of the flange seal is more resistant to shear stresses than the second zone residing near the inner edge of the flange seal. This arrangement reduces the likelihood of the flange seal being torn during use of the sanitary absorbent article.

25 Claims, 3 Drawing Sheets

SANITARY ABSORBENT ARTICLE HAVING A TEAR-RESISTANT FLANGE SEAL

FIELD OF THE INVENTION

The present invention relates to sanitary absorbent articles such as feminine sanitary napkins and incontinence pads, and, more particularly, to sanitary absorbent articles having a flange seal that is resistant to tearing.

BACKGROUND OF THE INVENTION

Sanitary absorbent articles are, generally, large-scale commercially manufactured articles used to absorb and retain bodily exudates. Such articles are convenient in that they are often economical yet disposable; they include sanitary napkins, infant diapers, adult incontinence pads and the like.

The technology surrounding sanitary absorbent articles, and particularly feminine sanitary napkins, has undergone several advances over the past two decades. One of such advances was the addition of a flap projecting laterally from each longitudinal side of the article when the article is in a flattened state. Such flaps may be comprised of integral extensions of a material from which the article is formed or, alternatively, may simply be comprised of additional material added to the article after its formation.

When such articles are in use, the flaps are folded over the edges of the wearer's undergarment. They thus may more firmly secure the article to the undergarment, stabilize the article within the undergarment, provide an increased absorptive area for bodily exudates, and help prevent the undergarment from becoming soiled in part by protecting the side edges of the wearer's undergarment. The flap concept has generally met with success in the marketplace, and articles with flaps of various configurations and conformations are available to the consumer.

Conventional wisdom on the part of both designers and consumers has to date dictated that flaps on absorbent articles should be maximized at their area of juncture with the main body of the article in order to provide a greater area of protection against exudate leakage over the side of the article. Hence, a very common flap configuration is an isosceles (i.e. bilaterally symmetrical) trapezoidal-shaped flap having its base adjoined with the longitudinal side portion of the main body of the article and projecting (and tapering) away therefrom to the top of the trapezoid. The size of the flap may vary from article to article.

The difficulty with absorbent articles of the trapezoidal and other conventional flap configurations is that the absorbent articles are designed and manufactured in a flat state, while in use the article should generally adopt a two- and often three-dimensional curvature in order to correctly interface with the body of the wearer. By two-dimensional curvature it is meant that the article will curve along one axis of the three-dimensional coordinate system formed by the longitudinal centerline of the article, the transverse centerline of the article, and the line perpendicular to both. By three-dimensional curvature it is meant that the article will curve along more than one axis of a three-dimensional co-ordinate system (such a system having three orthogonal axes).

As an example, where the absorbent article is a feminine sanitary napkin, and is in use, a cross-section of the article in both the sagittal plane of the wearer's body (i.e. the longitudinal axis of the article) and the frontal or coronal plane of the wearer's body (i.e. the transverse axis of the article) would most likely be curved. The flaps, however, are generally designed to be folded about a linear folding axis commonly located along the line of juncture of the flap with the longitudinal side of the main body of the article. The difficulty with such a linear folding axis is that the edges of the wearer's undergarment, about which the flaps are folded, are curved. Moreover, the undergarment edges usually contain an elastic material for snugly securing the undergarment about the legs of the wearer. Depending on the force exerted by the elastic material, a curved shape may be imparted to the flaps and the central portion of the main body of the article causing them to lift off the undergarment and wrinkle, or a flattened shape may be imparted to the edges of the undergarment causing them to not fit snugly against the legs of the wearer. In both cases, the comfort and efficiency of the article and its flaps are compromised. Moreover, the larger the flap, the more acute the problem. Thus while large flaps alleviate some difficulties on one hand (i.e. side leakage protection), they create problems on the other (i.e. instability and stress).

In order to alleviate the difficulties of conventional flap designs, a sanitary napkin has been proposed featuring flaps characterized by a width (dimension measured along the longitudinal axis of the sanitary napkin) that increases in a direction away from the main body of the napkin. This flap design offers a number of advantages, an important one being to securely retain the sanitary napkin to the undergarment of the wearer. Such enhanced retention is desirable because it stabilizes the sanitary napkin against the body of the wearer and thus reduces the likelihood of failure events.

It has been observed, however, that such strong attachment ability of the flaps may cause the flaps to tear apart from the main body when the sanitary napkin is removed from the undergarment. Usually, the wearer will not detach the flaps from the undergarment before lifting away the main body. The tendency is to simply pull the main body while the flaps remain attached to the undergarment. This manipulation creates stress levels on the sanitary napkin at the area of juncture main body/flap, often causing the flaps to tear and separate from the main body. This is undesirable since the wearer must then remove the separated flap(s) in a subsequent operation that may cause annoyance.

When the sanitary napkin tears, the tear usually originates in the peripheral area of the sanitary napkin that is called the "flange seal". The flange seal is an area of juncture between two component layers of the sanitary napkin. Typically, the cover layer and the liquid-impervious barrier layer of the sanitary napkin (their respective functions will be described later in this specification) are joined together to enclose, at least partially, the absorbent system of the sanitary napkin. The junction between the components that form the flange seal may be such that the components are directly united to one another or united to one another through one or more intermediate components.

Conventional manufacturing techniques employ a heat and pressure seal method that uses the application of pressure and/or heat to bond the layers of the sanitary napkin that form the flange seal. With this technique, the pressure applied on the layers forming the flange seal reduces the ability of the flange seal to resist shear stress. Without intent of being bound by a specific theory, this may be explained by the distortion that the materials of the layers forming the flange seal undergo during the heat and pressure seal operation. The high levels of pressure and heat have the effect of reducing the caliper of the layers to the point where the material is literally crushed which effectively reduces its ability to withstand shear stress.

When shear stress is applied to a flange seal formed by using a heat and pressure seal technique, having an order of magnitude observed when a sanitary napkin is removed by the wearer from the undergarment with the flaps still attached to the undergarment, it can produce a tear across the flange seal. The tear can then propagate to other components of the sanitary napkin, such as the flaps, and ultimately cause one or both flaps to separate from the main body of the sanitary napkin.

Considering this background, it clearly appears that there is a need in the industry to develop an improved flange seal for a sanitary absorbent article that can better resist shear stress by comparison to prior art flange seal configurations.

SUMMARY OF THE INVENTION

According to one broad aspect the invention provides a sanitary absorbent article comprising:

a main body, the main body having two opposing longitudinal side portions, two opposing transverse side portions, an imaginary longitudinal centerline and an imaginary transverse centerline, the main body including:

a fluid-pervious cover layer, the fluid-pervious cover layer facing towards a wearer's body when the sanitary absorbent article is in use by the wearer;

a liquid-impervious barrier layer, the liquid-impervious barrier layer facing away from the wearer's body when the sanitary absorbent article is in use by the wearer;

an absorbent system intermediate the fluid-pervious cover layer and the liquid-impervious barrier layer;

the fluid-pervious cover layer and the liquid-impervious barrier joined to one another to form a flange seal extending along at least a portion of the absorbent system;

at least a portion of the flange seal laying in an imaginary plane and including an outer edge and an inner edge, the inner edge residing closer to the absorbent system than the outer edge;

the portion of the flange seal laying in the imaginary plane including a first zone and a second zone separated from one another by a common boundary, an imaginary reference line laying in the imaginary plane and extending in a direction from the outer edge to the inner edge intersecting the first zone before intersecting the second zone; and the first zone manifesting a higher resistance to shear stress than the second zone.

In a non-limiting example of implementation, the longitudinal centerline of the article is an imaginary line that extends longitudinally along the main body of the article, which is equidistant from the longitudinal side portions thereof. It will thus bisect the main body into two generally mirror image halves. As the article is worn in the pudendal region, when the article is in use by a wearer, the longitudinal centerline thereof is generally parallel to, or most commonly, lies in, the sagittal plane of the wearer. The transverse centerline is an imaginary line that extends transversally across the article, and is typically, but not always, equidistant from the transverse sides thereof. The transverse centerline is perpendicular to the longitudinal centerline. Where the article has flaps (as described below), the transverse centerline is generally the line perpendicular to the longitudinal centerline that bisects the flaps.

The article is of a laminate construction and, under one non-limiting example of implementation, will have at least three layers. The first of these layers is the cover layer. The cover layer has two major surfaces, the first is an external surface (i.e. a surface that does not face another component layer of the article), which, when the article is in use by the wearer, faces the wearer's body. The other surface is an internal surface (i.e. a surface that faces another component layer of the article), which faces the absorbent system below. The cover layer is fluid-permeable, and thus will permit the body exudate to be absorbed by the article to pass through it into the layers below.

The absorbent system, positioned below the fluid-pervious cover layer, may comprise a single layer or multiple layers or additional structures, the primary purpose of all of which is to absorb and retain exudate. Many different absorbent systems are known in the art. The absorbent system has two major surfaces, both of which are internal surfaces, i.e. they both face other layers of the napkin. The first surface faces the fluid-pervious cover layer, the second surface faces the liquid-impervious barrier layer.

Underneath the absorbent system is the liquid-impervious barrier layer. The primary purpose of the liquid-impervious barrier layer is to prevent exudate absorbed within the napkin from egressing the absorbent article on the opposite side from which it was absorbed. The liquid-impervious barrier layer is thus impervious to liquid but could be made pervious to gases to provide breathability. The liquid-impervious barrier layer has two major surfaces, an external surface that faces the undergarment of the wearer when the napkin is in use, and an internal surface that faces the absorbent system.

Optionally, the article can be provided with a pair of flaps, one flap extending laterally from each longitudinal side portion of the main body thereof. Such flaps are flexible and are capable of being folded about the crotch portion of the undergarment of the wearer. The flaps serve several purposes, including stabilizing the article within the garment of the wearer and protecting the garment from being soiled by body exudate not absorbed and/or retained by the article.

Under the non-limiting example of implementation described above, the fluid-pervious cover layer and the liquid-impervious barrier layer are joined to one another along the periphery of the article to form a flange seal enclosing the absorbent system. It is advantageous, but not essential to the invention that the flange seal surround completely, and thus contain, the absorbent system within it. At least a portion of the flange seal includes a pair of zones separated by a common boundary, namely a first zone and a second zone, the first zone manifesting a higher degree of resistance to shear stress than the second zone. A "higher degree of resistance to shear stress" means that the first zone can tolerate a higher level of shear stress before tearing than the second zone.

Under the non-limiting example of implementation, the first and second zones are realized by creating on the flange seal regions distinguished from one another by the level of bonding between the fluid-pervious cover layer and the liquid-impervious barrier layer. The resistance to shear stress of a zone is dependent upon the level of bonding between the fluid-pervious cover layer and the liquid-impervious barrier layer at that zone. In particular, the inventors have observed that the resistance to shear stress varies inversely with the level of bonding achieved between the fluid-pervious cover layer and the liquid-impervious barrier layer. In a specific example of implementation, the fluid-pervious cover layer and the liquid-impervious barrier layer manifest a stronger bond at the second zone than at the first zone. The expression "stronger bond" or any other equivalent terminology used in this specification means that a measurable difference exists between the degree of adhesion established between the fluid-pervious cover layer and the liquid-impervious barrier layer. This definition does not imply that the fluid-pervious cover layer and the liquid-impervious barrier layer are necessarily bonded to one another at both zones. Rather, embodiments where an actual bond between the fluid-pervious cover layer and the liquid-impervious barrier layer exists only in the second zone, while the fluid-pervious cover layer and the liquid-impervious barrier layer are unadhered to one another in the first zone, fall under the present inventive concept. Also note that the expression "fluid-pervious cover layer bonded to the liquid-impervious barrier layer" or any other equivalent terminology implies a direct bond between the fluid-pervious cover layer and the liquid-impervious barrier layer or a bond through one or more intermediate components.

The present invention covers realizations where the first and the second zones extend only over a limited portion of the flange seal. In a non-limiting example of implementation, the first zone and the second zone can be formed at portions of the flange seal that in use are subjected to significant levels of sheer stress and where protection against tearing is desired. When the sanitary absorbent article is a sanitary napkin, such portions can be the segments of the flange seal adjoining the juncture areas between the flaps and the main body. In another broad aspect, the invention also provides a sanitary absorbent article, comprising:

a first layer of material;
a second layer of material;
a flange seal at which the first layer of material is attached to the second layer of material in an overlapping relationship,
at least a portion of the flange seal laying in an imaginary plane and including a first edge portion and a second edge portion in a spaced apart relationship to the first edge portion;
the portion of the flange seal laying in the imaginary plane including a first zone and a second zone separated from one another by a common boundary, an imaginary reference line laying in the imaginary plane and extending in a direction from the first edge portion to the second edge portion intersecting the first zone before said second zone; and
the first zone manifesting a higher resistance to shear stress than the second zone.

In a yet another broad aspect the invention also provides a sanitary absorbent article, comprising:

a first layer of material;
a second layer of material;
a flange seal at which the first layer of material is attached to the second layer of material in an overlapping relationship,
at least a portion of the flange seal being characterized by strong bond areas separated from one another by weak bond areas, the weak bond areas being characterized by a geometrical extension along a predetermined direction.

BRIEF DESCRIPTION OF THE DRAWINGS

A detailed description of preferred embodiments of the present invention is provided hereinbelow with reference to the following drawings, in which.

Figure 1:
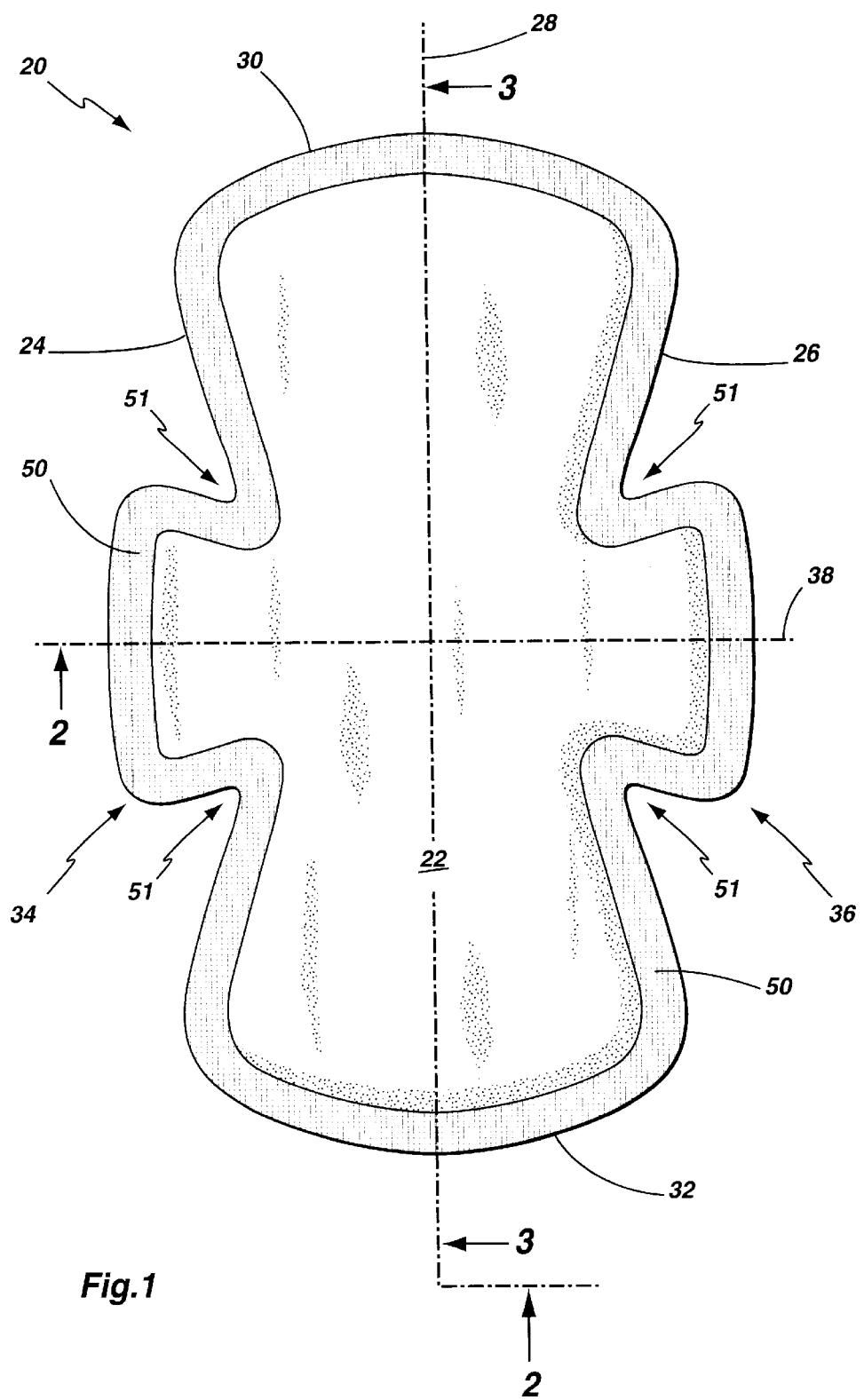
FIG. 1 is a top plan view of a first non-limiting example of implementation of the present invention in the form of a sanitary napkin.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION OF PREFERRED EMBODIMENTS

With reference to FIG. 1, there is shown a non-limiting example of implementation of a sanitary absorbent article, a disposable sanitary napkin 20. The napkin 20 comprises a main body 22. The main body 22 has two generally opposing longitudinal side portions 24, 26, and an imaginary longitudinal centerline 28 running down the center of the napkin 20, generally equidistant from the longitudinal side portions 24, 26. The longitudinal side portions 24, 26 are concavely arcuate.

The main body 22 also has two generally opposing transverse side portions 30, 32. The transverse side portions are convexly arcuate. Projecting laterally from each of the longitudinal side portions 24, 26 of the main body 22 is a flap 34, 36 (respectively). The flaps 34, 36 are generally of the shape of an isosceles (i.e. bilaterally symmetrical) trapezoid, with the shorter of the two parallel sides thereof adjoining the longitudinal side portions 24, 26 of the main body 22 of the napkin 20. An imaginary transverse centerline 38 runs across the napkin 20, perpendicular to the longitudinal centerline 28, and bisects the flaps 34, 36.

Figures 2, 3:
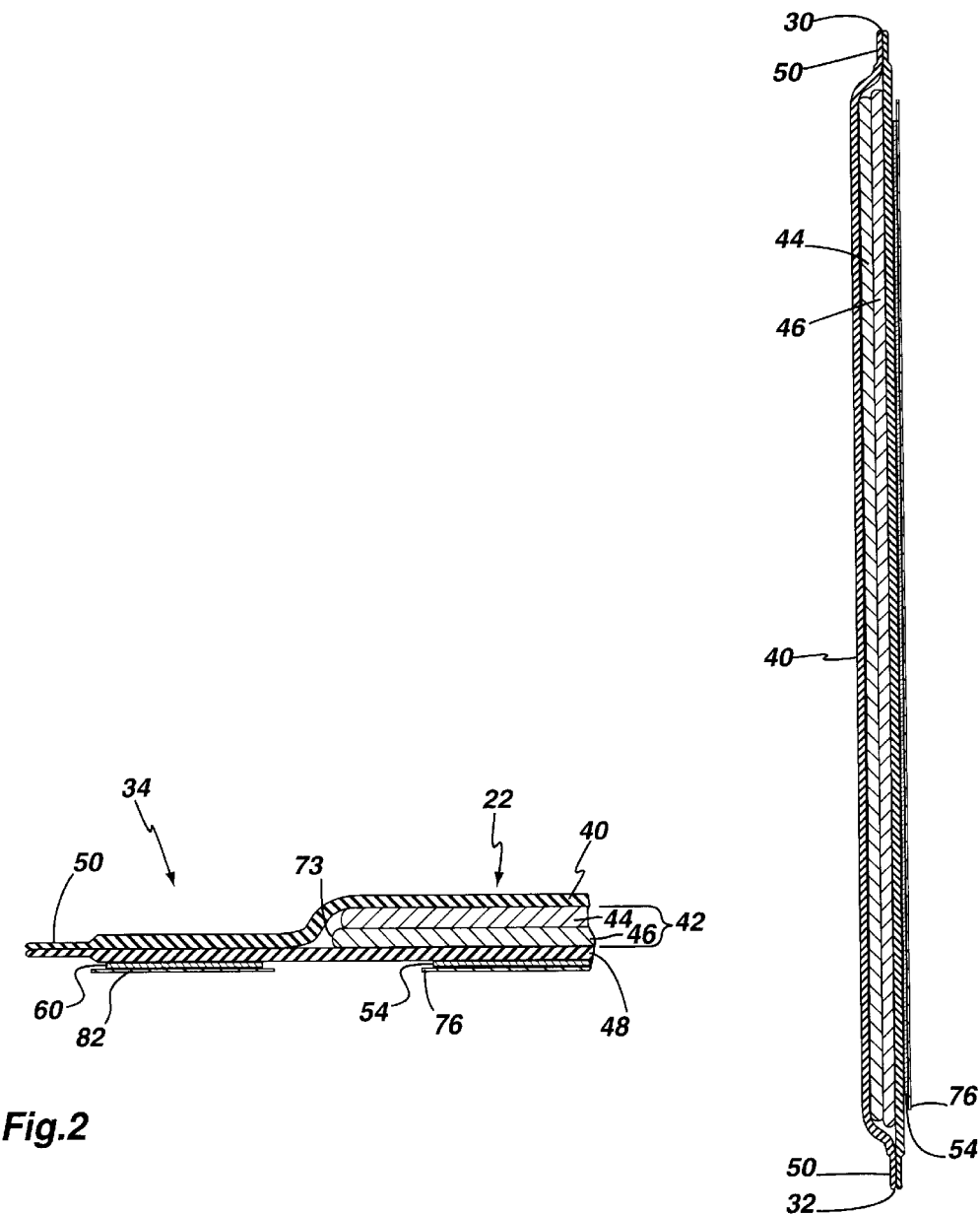
FIG. 2 is a cross-sectional view of the sanitary napkin taken along the line 2—2 in FIG. 1.
FIG. 3 is a cross-sectional view of the sanitary napkin taken along the line 3—3 in FIG. 1.

With reference to FIG. 2, the napkin 20 is a laminate structure and the main body 22 has a fluid-permeable cover layer 40 which will face the body of a wearer when the napkin 20 is in use; a liquid-impervious barrier layer 48, which will face the environment (i.e. away from the body of the wearer, and in almost all cases the wearer's undergarment) when the napkin 20 is in use; and an absorbent system 42 therebetween. The absorbent system 42 may have a single layer or multiple layers. In the example of implementation depicted in the drawings, a multiple layer structure is shown. More specifically, the absorbent system 42 has a first layer, called "transfer layer" 44 immediately underneath the fluid-pervious cover layer 40 and a second layer called "absorbent layer" 46 between the transfer layer 44 and the liquid-impervious barrier layer 48. The flaps 34, 36 are comprised of integral continuous extensions of the fluid-pervious cover layer 40 and the liquid-impervious barrier layer 48. Thus, the flaps 34, 36 are dual layer structures, the upper layer being a continuous extension of the fluid-pervious cover layer 40 while the bottom layer is a continuous extension of the liquid-impervious barrier layer 48. The flaps 34, 36 generally do not contain the absorbent system 42 therein. However, in an alternative embodiment not shown in the drawings, the absorbent system may extend into flaps or the flaps may be provided with separate absorbent layers. The fluid-pervious cover layer 40 and the liquid-impervious barrier layer 48 are sealed together along their peripheral edges (including the flaps 34, 36) to form a peripheral flange seal 50, containing the absorbent system 42. The flange seal 50 extends continuously around the absorbent system 42 to completely enclose the same. However, the present invention also covers embodiments where the flange seal 50 does not necessarily enclose completely the absorbent system 42. In the example depicted in FIG. 1, the flange seal 50 encloses completely the main body 22 and also encloses each individual flap 34, 36. Thus, a variety of flange seal configurations are within the scope of this invention.

Each of these layers will be described in further detail below.

Fluid-pervious Cover Layer

With reference to FIG. 1 through 3, the fluid-pervious cover layer 40 is the top layer of the sanitary napkin 20. The purpose of the fluid-pervious cover layer 40 is to provide an interface that would normally contact the body of the wearer when the sanitary napkin 20 is in use. The cover layer 40 is porous to liquids since its main function is to capture as quickly as possible a discharge of bodily exudate and transfer it to the absorbent system 42 underneath.

Under one specific example of implementation, the fluid-pervious cover layer 40 is formed from an apertured thermoplastic film. Such films are common in the art. An example is the co-extruded film described in U.S. Pat. No. 4,690,679, and marketed as RETICULON™ brand on sanitary napkins available from Johnson & Johnson Inc. of Montreal, Canada. Because of the high porosity of such films, they accomplish the function of quickly transferring body exudate to the inner layers (i.e. the absorbent system 42) of the napkin 20.

The fluid-pervious cover layer 40 can also be made of fibrous materials, such as non-woven fibrous materials. The fluid-pervious cover layer 40 may be composed of only one type of fiber, such as polyester, or may be composed of bicomponent or conjugate fibers having a low melting point component and a high melting point component. Bicomponent fibers may be made up of a polyester core and a polyethylene sheath. The use of appropriate bicomponent materials results in a fusible non-woven fabric. Examples of such fusible fabrics are described in U.S. Pat. No. 4,555,430. Using a fusible fabric increases the ease with which the fluid-pervious cover layer 40 may be mounted to the barrier layer 48 at the flange seal area 50.

The fibers may be selected from a variety of natural and synthetic materials such as nylon, polyester, rayon (in combination with other fibers), cotton acrylic fiber and the like and combinations thereof. An example is the multi-denier fluid-pervious cover layer described in the U.S. Pat. No. 6,087,551 assigned to Johnson & Johnson.

It will be evident to the person skilled in the art that a wide variety of other types of non-woven fabric materials can also be used.

Transfer Layer

Adjacent to the fluid-pervious cover layer 40 on its inner side and bonded thereto is an optional fluid transfer layer 44, that may form part of the absorbent system 42. The transfer layer 44 provides the means of receiving body fluid from the fluid-pervious cover layer 40 and holding it until the highly-dense absorbent layer 46 has an opportunity to absorb it.

The transfer layer 44 is, preferably, more dense than and has a larger proportion of smaller pores than the fluid-pervious cover layer 40. These attributes allow the transfer layer 44 to contain body fluid and hold it away from the outer side of the fluid-pervious cover layer 40, thereby preventing the fluid from re-wetting the fluid-pervious cover layer 40 and its surface. However, the transfer layer 44 is, preferably, not so dense as to prevent the passage of the fluid through the transfer layer 44 and into the absorbent layer 46 therebelow.

The transfer layer 44 may be composed of fibrous materials, such as wood pulp, polyester, rayon, flexible foam, or the like, or combinations thereof. The transfer layer 44 may also comprise thermoplastic fibers for the purpose of stabilizing the layer and maintaining its structural integrity. The transfer layer 44 may be treated with surfactant on one or both sides in order to increase its wettability, although generally the transfer layer 44 is relatively hydrophilic and may not require treatment. The transfer layer 44 is preferably bonded on both sides to the adjacent layers, i.e. the fluid-pervious cover layer 40 and the absorbent layer 46. An example is the material sold by Merfin in the United-States under the commercial designation VICELL 6002.

Absorbent Layer

Immediately adjacent to and bonded to the transfer layer 44 is the absorbent layer 46 that forms part of the absorbent system 42. The absorbent system 42 may comprise only the absorbent layer 46 or it may comprise a plurality of layers, such as the absorbent layer 46 in combination with the transfer layer 44 or any other additional layer. This is to say that the transfer layer 44 is not an essential component of the present invention.

The absorbent layer 46 is a highly dense layer having a fine porosity. It has a large liquid-holding capacity and it is extremely retentive. Preferably, the absorbent layer 46 comprises a pulp fluff material and may optionally include other absorbent materials or non-absorbent materials such as conjugate fibers, fusible fibers, binders, sphagnum moss, superabsorbents, and the like and combinations thereof. A suitable absorbent layer 46 is described in the U.S. Pat. No. 5,866,242 granted on Feb. 2, 1999 to Tan et al. The contents of this document are hereby incorporated by reference.

The absorbent system 42 has two longitudinal sides 73 (only one is shown in the Figures notably in FIG. 2), each of which is generally parallel to the longitudinal side portions 24, 26 of the main body 22 of the napkin 20. Where the absorbent system 42 comprises a composite laminate structure (as opposed to a single layer), the longitudinal sides 73 thereof should be considered to be the longitudinal sides of the component thereof having the largest width, as measured along the transverse centerline 38 of the article.

Liquid-impervious Barrier Layer

Underlying the absorbent system 42 is a liquid-impervious barrier layer 48 comprising liquid-impervious film material to prevent liquid that is entrapped in the absorbent layer 46 from egressing the sanitary napkin 20 and staining the wearer's undergarment. The liquid-impervious barrier layer 48 can be made of polymeric film, such as polyethylene or a polyethylene/ethylvinyl acetate (EVA), which are both inexpensive and readily available. The polymeric film is capable of fully blocking the passage of liquid or gas that may emanate from the absorbent system 42. In a variant, breathable films may be used that allow passage of gases while blocking liquid. A suitable example is a combination polyethylene/ethylvinyl acetate (EVA) film sold by the Edison Plastics Company in the United States under the commercial designation XP-1167B.

Flange Seal

Figure 4:
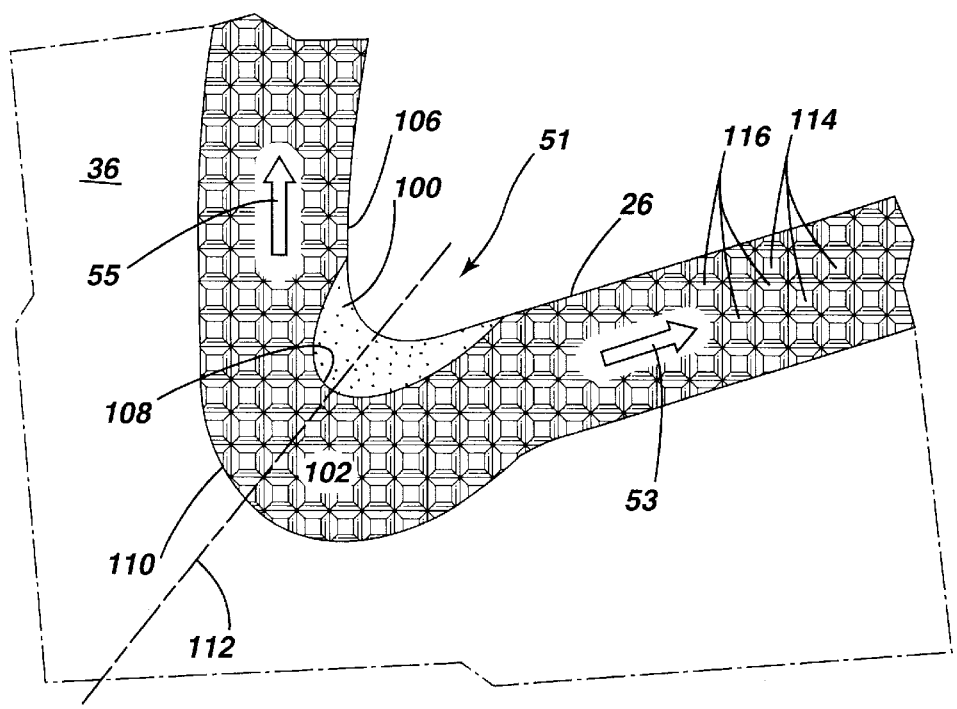
FIG. 4 is an enlarged fragmentary top plan view of the sanitary napkin shown in FIG. 1, illustrating a portion of the flange seal combining zones manifesting different levels of resistance to shear stress.
Figure 5:
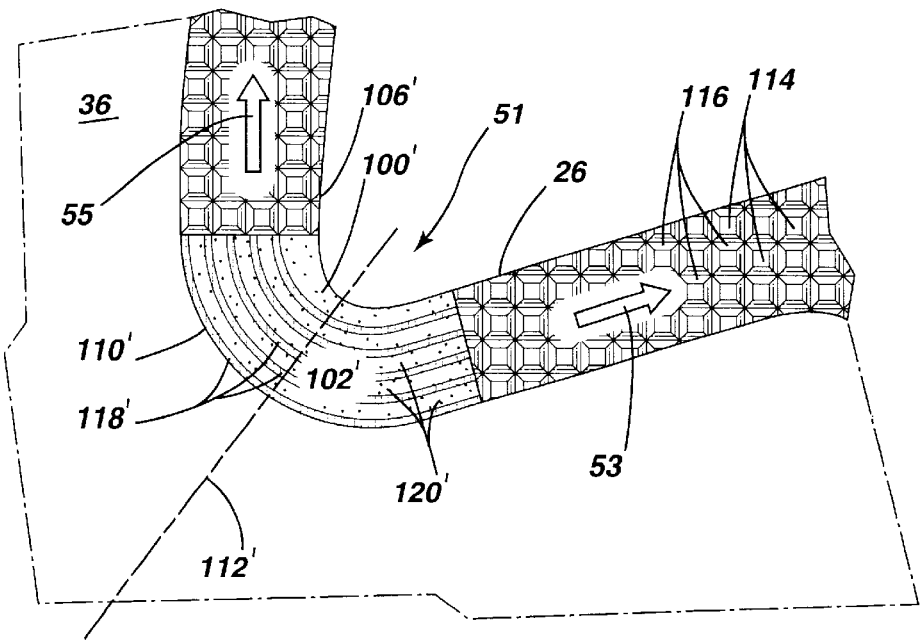
FIG. 5 depicts a variant of the flange seal shown in FIG. 4.

The structure of the flange seal 50 will now be described in connection with FIGS. 1, 4 and 5 of the drawings. In the example of implementation depicted in FIG. 1, the flange seal 50 lays in an imaginary plane that bisects the main body 22 of the sanitary napkin in two superimposed parts. This planar arrangement of the flange seal 50 occurs when the sanitary napkin is laying flat on a planar surface. FIG. 4 illustrates a portion of the flange seal 50 in the area of juncture between the flap 36 and the longitudinal side 26. At the base of the flap 36 is found an area of juncture, which is generally the place where the flap connects with the main body 22. In general, the area of juncture is parallel to the longitudinal centerline 28 and has two extremities, each extremity coinciding with a corner-like area at which the flange seal 50 makes a sharp bend. In FIGS. 1, 4 and 5, the bends that mark the extremities of the areas of juncture are denoted by the reference numeral 51. At that location, the flange seal 50 is provided with two zones manifesting different mechanical properties. More specifically, the flange seal 50 comprises a first zone 100 and a second zone 102. The first zone 100 is bounded at one end by a concave outer edge portion 106 of the flange seal 50 and a common boundary 108 at the other end that forms a border or limit between the first zone 100 and the second zone 102. The common boundary is formed by a combination of arcs of circle having different radii. In particular, the shape of the common boundary is analogous to the end portion (along the long axis) of an ellipse.

The second zone 102 is defined between the common boundary 108 and a convex inner edge portion 110 of the flange seal 50. The inner edge portion 110 is adjacent the absorbent system 42 while the outer edge portion 106 is remote from the absorbent system 42. The geometrical relationship between the first zone 100 and the second zone 102 is such that when an imaginary reference line 112 (dotted line in FIG. 4) is located within the imaginary plane containing the flange seal 50 such as to extend from the outer edge portion 106 to the inner edge portion 110 of the flange seal 50, the imaginary line of reference 112 will cross the outer edge portion 106, then intersect the first zone 100, followed by the common boundary 108, followed by the second zone 102 and finally the inner edge portion 110.

The first zone 100 is characterized by an ability to better resist shearing stress than the second zone 102. In other words, the first zone 100 can be subjected to a higher level of shearing stress than the second zone 102 before a tear appears. One practical way to demonstrate that the first zone 100 has a higher resistance to shearing stress than the second zone 102 is to conduct the following test on the sanitary napkin 20 shown in FIG. 4. The flange seal 50 is subjected to a pulling effort having a tendency to open-up the bend 51. This can be achieved by applying tension on the flange seal at two locations on either side of the bend 51 and in opposite directions, as shown by the tension vectors 53 and 55. The tension is increased until a fissure or tear begins to appear at the outer edge portion 106. The level of tension is recorded. The same experiment is repeated but this time the flange seal is modified to eliminate the first zone 100. In other words, the second zone 102 extends completely from the outer edge portion 106 to the inner edge portion 110. No other changes are made to the sanitary napkin 20. The level of tension that must be applied in the later case to start a fissure or tear should be less than the level of tension in the former case.

Under one specific example of implementation, the first and the second zones 100, 102 are realized by creating on the flange seal 50 regions distinguished from one another by the level of bonding between the fluid-pervious cover layer 40 and the liquid-impervious barrier layer 48. In particular, the fluid-pervious cover layer 40 and the liquid-impervious barrier layer 48 are bonded to one another by a using a heat and pressure seal operation based on a knurl pattern at the second zone 102 which is such that the fluid-pervious cover layer 40 and the liquid-impervious barrier layer 48 are united to one another in a manner that does not permit the separation of the layers without destroying them. In other words, the bonding between the layers is permanent. It is not deemed necessary to describe in detail the heat and pressure seal operation since this bonding method is well known in the art. Suffice it to say that the method is performed by applying both pressure and heat to the fluid-pervious cover layer 40 and the liquid-impervious barrier layer 48 to cause them to adhere to one another. In the example illustrated in FIG. 4, the pressure is applied according to a knurl pattern that includes an array of generally rectangular areas 114, separated from one another by a network of crossing lines 116. The rectangular areas 114 define strong bond areas where the fluid-pervious cover layer 40 and the liquid-impervious barrier layer 48 are intimately bonded to one another. In contrast, the network of crossing lines 116 define weak bond areas at which the attachment between the fluid-pervious cover layer 40 and the liquid-impervious barrier layer 48 is weaker than at the areas 114. The second zone 102 therefore comprises an array of discontinuous strong bond areas that collectively retain the fluid-pervious cover layer 40 and the liquid-impervious barrier layer 48 to one another in a way to prevent them from separating.

The process conditions necessary to form the heat and pressure seal at the second zone 102, in particular the temperature, the level of pressure and amount of time during which the pressure and the heat are applied, will vary according to the type of materials being bonded. It is within the reach of a person skilled in the art to select the proper process conditions to suit the intended application. The apparatus that could be used for conducting the heat and pressure seal operation is of a type well known to a person skilled in the art. Such apparatus comprises a pair of sealing rolls (not shown in the drawings) between which the flange seal 50 passes to achieve the bonding at the second zone 102. One of the rolls has a surface engraved according to the knurl pattern. More particularly, the roll has on its surface an array of projecting rectangles, where each rectangle corresponds to an area 114, the rectangles being separated from one another by void areas corresponding to the network of crossing lines 116. The other roll, a so-called anvil roll supports the materials forming the flange seal 50 when the engraved roll applies pressure on them. One or both of the rolls are heated to elevate the temperature of the materials forming the flange seal 50 during the bonding operation. During the passage of the flange seal 50 between the rolls, the pressure is applied only by the projecting rectangles to form the areas 114, while the voids between the projecting rectangles apply no pressure to the materials of the flange seal resulting in the network of crossing lines 116. In a very specific example of implementation, each rectangle has sides of about 0.4 millimeters (mm) long and the distance between opposing sides of adjacent rectangles is of about 0.6 mm.

In light of the fact that the network of crossing lines 116 corresponds to areas of the flange seal 50 at which little or no pressure is applied during the heat and pressure sealing operation, it follows that the heat and pressure sealing operation does not substantially change the level of bonding between the fluid-pervious cover layer 40 and the liquid-impervious barrier layer 48 at the network of crossing lines 116 from what existed before the heat and pressure sealing operation is conducted. It has been found advantageous to adhesively bond the fluid-pervious cover layer 40 and the liquid-impervious barrier layer 48 to one another before conducting the heat and pressure sealing operation. This allows to create an adhesive bond between the fluid-pervious cover layer 40 and the liquid-impervious barrier layer 48 at the network of crossing lines 116 (weak bond areas) that will remain after the heat and pressure sealing operation is performed. Alternatively, the fluid-pervious cover layer 40 and the liquid-impervious barrier layer 48 are unaffixed to one another such that after the heat and pressure sealing operation, no bond exists at the network of crossing lines 116 (weak bond areas).

FIG. 4 shows the knurl pattern as being formed of rectangles. Alternatively, lozenges, or other shapes instead of rectangles can be used.

The use of a heat and pressure seal operation to form the second zone 102 is not an essential element of the invention because alternative bonding methods for forming the second zone 102 can also be used. For example, the second zone 102 may be formed by using ultrasonic bonding, radio frequency sealing, mechanical crimping, and the like and combinations thereof. Also, the knurl pattern is not an essential element of the invention as other patterns can be used without departing from the spirit of the invention.

The fluid-pervious cover layer 40 and the liquid-impervious barrier layer 48 manifest a stronger bond at the second zone 102 than at the first zone 100. Two possibilities can exist in this regard. Under the first possibility, the fluid-pervious cover layer 40 and the liquid-impervious barrier layer 48 are adhesively bonded at the first zone 100, however, the bond is weaker than the bond at the second zone 102. Under the second possibility, the fluid-pervious cover layer 40 and the liquid-impervious barrier layer 48 are not bonded to one another at the first zone 100.

The first possibility where the fluid-pervious cover layer 40 and the liquid-impervious barrier layer 48 are adhesively bonded at the first zone 100 is preferred over the second possibility.

The first and the second zones 100 and 102 are realized at the same time on the flange seal 50. In particular, the heat and pressure sealing operation is conducted in such a manner as to avoid application of pressure at the area of the flange seal 50 where the first zone 100 is created. Similar to the approach used for creating the network of crossing lines 116, the roll that applies the pressure on the flange seal is shaped in a way such as to present a void area where the first zone 100 is to reside on the flange seal 50. The adhesive to create the bond between the fluid-pervious cover layer 40 and the liquid-impervious barrier layer 48 at the network of crossing lines 116 and at the first zone 100 is applied between the layers by any suitable method before the heat and pressure sealing operation is conducted.

In a very specific example of implementation, the first zone 100 has a surface area of at least 20 mm$^2$ and preferably of about 30 mm$^2$. Also, the first zone 100 has a geometrical configuration such that the maximal distance that can be measured between the outer edge portion 106 to the common boundary 108 is of at least X where X is in the range from about 2 mm to about 10 mm and more preferably in the range from about 3 mm to about 6 mm. The maximal distance is established by laying an imaginary reference line that crosses the outer edge portion 106 and the common boundary 108. The positions at which the imaginary line crosses the outer edge portion 106 and the common boundary 108 are selected such that the distance between the crossing points is the greatest distance that can be found, while the imaginary line intersects the first zone 100.

Under this very specific example of implementation, the flange seal 50 has a width at the bend 51 in the range from about 3 mm to about 12 mm. Preferably, the width of the flange seal at the bend 51 is of about 6 mm.

FIG. 5 shows another embodiment of the flange seal 50 which also has a first zone 100' and a second zone 102'. The second zone 102' includes strong bond areas 118' between the fluid-pervious cover layer 40 and the liquid-impervious barrier layer 48 that have a geometrical extension along a preferential direction. In the example shown in the drawings, the strong bond areas 118' are linear, and in particular curvilinear. More specifically, the strong bond areas 118' are parallel and follow the contour of the inner edge portion 110'. The strong bond areas 118' are separated from one another by weak bond areas 120' at which the fluid-pervious cover layer 40 and the liquid-impervious barrier layer 48 are either not bonded to one another or are more weakly bonded to one another relative to the strong bond areas 118'. The weak bond areas 120' are curvilinear, parallel to one another and they alternate with the strong bond areas 118'.

Without intent of being bound by a certain theory, the present inventors infer that the second zone 102' should normally exhibit a higher resistance to shear stresses than the second zone 102. This assumption is based on the fact that the second zone 102' exhibits weak bond areas 120' that are significantly larger than the weak bond areas 116 in the second zone 102.

Advantageously, the thickness of the strong bond areas 118' is of about 0.4 mm, while the thickness of the weak bond areas 120' is of about 0.6 millimeters.

The second zone 102' is realized by a heat and pressure seal operation as described earlier where the engraved roll that applies the pressure has a relief surface to create the succession of the strong bond areas 118' and the weak bond areas 120'.

The examples of implementation of the invention shown in FIGS. 1, 4 and 5 possess a flange seal 50 having a combination of a first zone 100, 100' and a second zone 102, 102' located adjacent each extremity of an area of juncture between a flaps 34, 36 and the main body 22 of the sanitary napkin 20. Those extremities generally coincide with the bends 51. These are advantageous locations since those specific areas of the flange seal 50 are subjected to high shear stress levels, particularly when the user attempts to remove the sanitary napkin 20 from the undergarment by pulling on the sanitary napkin 20 without previously detaching the flaps 34, 36. It should also be appreciated that the combination first zone 100, 100' and second zone 102, 102' can be placed at any other suitable location on the flange seal 50 where protection against tearing is desirable.

Adhesives

Referring to FIG. 2 and 3, in order to secure the napkin 20 to the undergarment of a wearer, the liquid-impervious barrier layer 48 is provided with two areas of standard adhesive material 54 and 60("adhesives") on the environmental (i.e. undergarment) facing surface thereof. Specifically, one main adhesive 54 is located on the underside of the main body 22 of the napkin 20. Additionally, there is an adhesive located on each of the flaps 34, 36 (adhesive 60 on flap 34 in FIG. 2). A single standard release paper 76 covers the main adhesive 54 positioned on the underside of the main body 22 while the flaps 34, 36 are covered by release papers 82 and 84 respectively (I invented these numeral references.). A suitable adhesive is the composition designated HL-1491 XZP commercially available from H. B. Fuller Canada, Toronto, Ontario, Canada. The release papers are of conventional construction (silicone coated wet-laid Kraft wood pulp) and suitable papers are available from Tekkote Corporation (Leonia, N.J., USA), and bear the designation FRASER 30#/61629.

Applications of the product and methods of the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

We claim:

1. A sanitary absorbent article comprising:
    a main body, said main body having two opposing longitudinal side portions, two opposing transverse side portions, an imaginary longitudinal centerline and an imaginary transverse centerline, said main body including:
        a fluid-pervious cover layer, said fluid-pervious cover layer facing towards a wearer's body when the sanitary absorbent article is in use by the wearer;
        a liquid-impervious barrier layer, said liquid-impervious barrier layer facing away from the wearer's body when the sanitary absorbent article is in use by the wearer;
        an absorbent system intermediate said fluid-pervious cover layer and said liquid-impervious barrier layer;
    wherein said sanitary absorbent article includes at least one flap projecting laterally from a longitudinal side portion of said main body, said flap connecting with said main body through an area of juncture
    said fluid-pervious cover layer and said liquid-impervious barrier joined to one another to form a flange seal extending along at least a portion of a peripheral edge margin of said absorbent system;
    at least a portion of said flange seal laying in an imaginary plane in the area of juncture between the flap and the longitudinal side portion and including an outer edge portion and an inner edge portion, said inner edge portion residing closer to said absorbent system than said outer edge portion;
    the portion of said flange seal laying in said imaginary plane in the area of juncture between the flap and the longitudinal side portion including a first zone and a second zone separated from one another by a common boundary, an imaginary reference line laying in said imaginary plane and extending in a direction from said outer edge portion to said inner edge portion intersecting said first zone before said second zone; and
    said first zone manifesting a higher resistance to shear stress than said second zone.

2. A sanitary absorbent article as defined in claim 1, wherein said fluid-pervious cover layer and said liquid-impervious barrier layer manifest a stronger bond to one another at said second zone than at said first zone.

3. A sanitary absorbent article as defined in claim 2, wherein said imaginary reference line intersects said common boundary before intersecting said second zone.

4. A sanitary absorbent article as defined in claim 3, wherein said first zone is bound between said outer edge portion and said common boundary.

5. A sanitary absorbent article as defined in claim 4, wherein said outer edge portion includes a segment that forms a boundary of said first zone, said segment being concave.

6. A sanitary absorbent article as defined in claim 5, wherein said area of juncture including a first extremity and a second extremity, the portion of said flange seal including said first zone and said second zone being adjacent the first extremity of said area of juncture.

7. A sanitary absorbent article as defined in claim 6, wherein said first zone has a surface area of not less than about 20 $mm^2$.

8. A sanitary absorbent article as defined in claim 7, wherein said first zone has a surface area of not less than about 30 $mm^2$.

9. A sanitary absorbent article as defined in claim 5, wherein said first zone has a maximal dimension measured from said outer edge portion to said common boundary in the range from about 2 mm to about 10 mm.

10. A sanitary absorbent article as defined in claim 9, wherein said first zone has a maximal dimension measured from said outer edge portion to said common boundary in the range from about 3 mm to about 6 mm.

11. A sanitary absorbent article as defined in claim 5, wherein said fluid-pervious cover layer and said liquid-impervious barrier layer are bonded to one another at said second zone by the application of heat and pressure.

12. A sanitary absorbent article as defined in claim 11, wherein said second zone is characterized by strong bond areas separated from one another by weak bond areas.

13. A sanitary absorbent article as defined in claim 12, wherein said strong bond areas are characterized by a geometrical extension along a preferential direction.

14. A sanitary absorbent article as defined in claim 13, wherein said strong bond areas are linear.

15. A sanitary absorbent article as defined in claim 14, wherein said strong bond areas are curvilinear.

16. A sanitary absorbent article as defined in claim 15, wherein said strong bond areas are generally parallel to one another.

17. A sanitary absorbent article as defined in claim 15, wherein said strong bond areas extend along said inner edge portion.

18. A sanitary absorbent article as defined in claim 12, wherein said weak bond areas are characterized by a geometrical extension along a preferential direction.

19. A sanitary absorbent article as defined in claim 18, wherein said weak bond areas are linear.

20. A sanitary absorbent article as defined in claim 19, wherein said weak bond areas are generally parallel to one another.

21. A sanitary absorbent article as defined in claim 20, wherein said weak bond areas extend along said inner edge portion.

22. A sanitary absorbent article as defined in claim 21, wherein said strong bond areas are parallel to said weak bond areas.

23. A sanitary absorbent article as defined in claim 22, wherein said strong bond areas have a width of about 0.4 mm.

24. A sanitary absorbent article as defined in claim 23, wherein said weak bond areas have a width of about 0.6 mm.

25. A sanitary absorbent article as defined in claim 1, wherein the sanitary absorbent article is a sanitary napkin.

* * * * *